(12) United States Patent
Buffiere et al.

(10) Patent No.: US 9,410,974 B2
(45) Date of Patent: Aug. 9, 2016

(54) GEL CARD FILLING DEVICE COMPRISING AN IONIZER

(71) Applicant: BIO-RAD INNOVATIONS, Marnes la Coquette (FR)

(72) Inventors: Frédéric Buffiere, Pessac (FR); Serge Petit, Noailly (FR); Jean-Michel Brisebrat, Villers (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 0 days.

(21) Appl. No.: 14/861,233

(22) Filed: Sep. 22, 2015

(65) Prior Publication Data

US 2016/0011226 A1   Jan. 14, 2016

Related U.S. Application Data

(63) Continuation of application No. 13/263,394, filed as application No. PCT/FR2010/050602 on Mar. 31, 2010, now Pat. No. 9,146,249.

(51) Int. Cl.
| | | |
|---|---|---|
| *G01N 35/10* | (2006.01) | |
| *B65B 3/04* | (2006.01) | |
| *B65B 55/00* | (2006.01) | |
| *B65B 3/00* | (2006.01) | |
| *G01N 35/02* | (2006.01) | |

(52) U.S. Cl.
CPC .............. *G01N 35/1079* (2013.01); *B65B 3/04* (2013.01); *B65B 55/00* (2013.01); *B65B 3/006* (2013.01); *G01N 35/025* (2013.01); *G01N 35/026* (2013.01)

(58) Field of Classification Search
CPC . G01N 35/1079; G01N 35/026; G01N 35/10; G01N 21/11; G01N 2035/0405; B01L 3/0289; B01L 2300/816; B65B 3/04; B67B 7/24; Y10T 83/0481; H05F 1/00; H05F 1/02; H05F 3/00; H05F 3/06
See application file for complete search history.

(56) References Cited

U.S. PATENT DOCUMENTS

| | | |
|---|---|---|
| 5,780,248 A | 7/1998 | Milchanoski et al. |
| 6,162,399 A | 12/2000 | Martinell Gisper-Sauch |
| 7,470,547 B2 | 12/2008 | Tisone et al. |
| 8,021,611 B2 | 9/2011 | Roach et al. |

(Continued)

FOREIGN PATENT DOCUMENTS

| | | |
|---|---|---|
| CN | 1783607 A | 6/2006 |
| DE | 2151729 A1 | 4/1973 |

(Continued)

OTHER PUBLICATIONS

RU OA re appln 2011141735 issued by the Russian patent office on Mar. 18, 2014.

(Continued)

*Primary Examiner* — Brian R Gordon
(74) *Attorney, Agent, or Firm* — Morris & Kamlay LLP

(57) ABSTRACT

A device for filling at least one receptacle (12) of gel card type initially sealed by a cap. The filling device comprises a piercing member (110) for perforating the cap, an ionization ramp (122) for eliminating the electrostatic charges capable of being borne by the receptacle, and filling means (130) one or more pipettes (132) for filling the receptacle after perforation of the cap and elimination of the electrostatic charges.

9 Claims, 4 Drawing Sheets

(56) References Cited

U.S. PATENT DOCUMENTS

| | | |
|---|---|---|
| 2001/0039977 A1 | 11/2001 | Sharon |
| 2002/0001544 A1 | 1/2002 | Hess et al. |
| 2009/0071245 A1* | 3/2009 | Harazin ................ G01F 23/266 73/290 R |
| 2009/0081081 A1 | 3/2009 | Kowari et al. |

FOREIGN PATENT DOCUMENTS

| | | |
|---|---|---|
| EA | 200702255 A1 | 4/2008 |
| JP | 62-148858 | 7/1987 |
| JP | 02-040562 | 2/1990 |
| JP | 6-18968 | 3/1994 |
| JP | 11-108937 | 4/1999 |
| RU | 2341804 C2 | 12/2008 |

OTHER PUBLICATIONS

Japanese Patent Office, "Notification of Reasons for Refusal", in Patent Application No. 2012-504048, Jul. 23, 2013.

* cited by examiner

GEL CARD FILLING DEVICE COMPRISING AN IONIZER

CROSS-REFERENCE TO RELATED APPLICATIONS

This is a continuation application of U.S. application Ser. No. 13/263,394, filed Nov. 9, 2011 (now issued as U.S. Pat. No. 9,146,249), which is a National Phase application of PCT Application Serial No. PCT/FR2010/50602, filed Mar. 31, 2010, which is an international application of French Appl. No. 0952290, filed on Apr. 8, 2009 (now issued as FR2944263), each of which is incorporated by reference in their entirety.

The present invention relates to the field of devices for performing medical analyses.

BACKGROUND

Traditionally, such devices, also called analysis machines, make it possible to automate certain protocols, such as for example pipetting liquids into gel cards. This protocol consists of pouring a predetermined quantity of liquid into a reactive well of a gel card containing one or more reagents. This liquid can for example be a blood sample, or any other type of human sample.

In a known manner, a gel card is a receptacle containing one or more reactive wells that are initially sealed by a cap. After having pierced the cap and poured the liquid, chemical reactions occur between the poured liquid and the reagent(s) of the card.

Generally, the quantity of liquid poured is very small, in the vicinity of several microliters, so that one generally refers to a "dose." What is more, the filling of the wells must respect certain quality criteria. Among these criteria, we will more particularly mention those relative to the creation of an air gap between the dose of liquid dispensed into the well and the reagent previously present at the bottom of the well, as well as the criterion relative to the absence of liquid splashes on the inner wall of the well. Splashes most often come from more or less significant, but still random, fracturation of the dispensed dose of liquid.

The presence of an air gap has the effect of provisionally prohibiting physical contact between the dispensed dose of liquid and the reagent. One interest is of controlling the moment from which the chemical reaction must begin. In practice, the gel cards are incubated and centrifuged after dispensing the liquid dose thereby leading to the chemical reaction.

The absence of splashes in turn is necessary in order to prevent a fraction of the dose of liquid from remaining stuck to the walls of the well and thus being removed from the incubated and centrifuged reactive mixture.

To resolve the first problem, document U.S. Pat. No. 5,780,248 proposes the use of consumable accessories made from plastic, said accessory being formed by an insert provided with six cavities with a pointed lower end. Moreover, the lower ends of the cavities are provided with a very small hole. This accessory is intended to be manually planted in a gel card, the ends of the cavities perforating the cap sealing the wells of the gel card. Each of the cavities of the accessory is housed in a well of the gel card. Then, a dose of liquid is dispensed into each of the cavities of the accessory. Using that accessory, the operator does not need to worry about whether an air gap is formed, inasmuch as the cavity isolates the dispensed liquid dose from the reagent contained at the bottom of the well. It also appears that the use of such accessories makes it possible to decrease the presence of splashes.

However, this solution has several drawbacks: the accessories must be purchased, stored and handled. What is more, the installation of the accessories on the gel cards must necessarily be done manually, which is inconvenient and not very fast.

BRIEF SUMMARY

One aim of the present invention is to propose a device for filling at least one receptacle of the gel card type initially sealed by a cap, allowing automatic filling while resolving the aforementioned drawbacks.

The invention achieves its aim by the fact that the filling device includes a piercing member to perforate the cap, means for eliminating the electrostatic charges that may be borne by the receptacle, and filling means to fill the receptacle after perforation of the cap and elimination of the electrostatic charges.

The inventors have in fact noted that the elimination of the electrostatic charges on the receptacle makes it possible to clearly avoid the formation of splashes on the inner walls of the receptacle. In fact, it happens that the electrostatic charges borne by the receptacle tend to dislocate the liquid dose when it leaves the filling means. It follows that certain fractions of the dose adhere against the inner wall of the receptacle, due to the attraction forces created by the electrostatic charges.

It is therefore understood that the filling device according to the invention advantageously makes it possible to prevent splashes from forming. Furthermore, the present invention does not require the use of consumables, unlike the prior devices. Another interest of the present invention is that it allows automatic filling.

What is more, the formation of the air gap is favored by the absence of electrostatic force tending to deflect the dose released by the filling means.

Preferably, the receptacle is a card, of the gel card type, which includes a plurality of wells sealed by the cap, each of the wells containing one or more reagents.

Advantageously, the piercing member includes a piercing rake provided with a plurality of piercing tips that are intended to penetrate the wells while passing through the cap.

One interest of the rake is that it makes it possible to pierce several holes in the cap all at once, these holes being those through which the filling means pour the liquid into the wells.

Preferably, the rake includes as many tips as the number of wells of the gel card, as a result of which the operation for piercing the cap of a gel card is performed a single time.

Particularly advantageously, the means for eliminating the electrostatic charges comprise an ionizer. The latter generates a flow of alternatingly positively and negatively charged ions, this ion flow being sent toward the receptacle, preferably after the cap has been perforated. This alternation makes it possible to eliminate the electrostatic charges borne by the wells of the gel card.

Preferably, the ionizer can and is intended to generate an electrical field producing a corona effect. Said corona effect, known in itself, is also called crown effect.

According to one preferred embodiment, the filling device has an intake direction for the receptacles toward the piercing member and the ionizer is made up of at least one ionization ramp extending transversely relative to said intake direction. Said ramp is preferably arranged as close as possible to the piercing zone in order to ionize the gel card right after the cap is pierced.

Furthermore, the ionizer preferably includes a plurality of electrodes targeting a zone in which the receptacle is intended to be located during piercing of the cap of said receptacle.

Without going beyond the scope of the present invention, it would also be possible to use an ionizer provided with means for blowing ionized air toward the gel card.

Preferably, the ionization ramp extends between the two mobile arms that bear the piercing rake, owing to which it is possible to ionize the gel card immediately after the piercing operation.

The invention also relates to a medical analysis machine to analyze the chemical reactions taking place in at least one receptacle that comprises a plurality of wells containing one or more reagents while being sealed by at least one cap, said machine including a filling device according to the invention, means for bringing said receptacle toward said filling device, and means for analyzing the chemical reactions that can occur in the wells of the receptacle after the filling means have poured a quantity of liquid into each of the wells.

The machine preferably includes a plurality of receptacles made up of similar or different gel cards.

Advantageously, the machine according to the invention also includes a checking station to verify the positioning of the liquid poured into the wells by the filling means.

Preferably, said checking station includes a camera as well as image processing means making it possible to identify the presence or absence of an air gap and any splashes.

The invention also relates to a method for filling a receptacle of the gel card type provided with a plurality of wells sealed by a cap, comprising:
- a step of piercing the cap of the receptacle in order to open the wells;
- a step of eliminating electrostatic charges that may be borne by the receptacle; and
- a filling step during which a quantity of liquid is poured into each of the wells of the receptacle.

Preferably, this method is implemented by the filling device according to the present invention.

Advantageously, the step of eliminating the electrostatic charges consists of ionizing the wells of the receptacle by generating an electrical field producing a corona effect.

Preferably, but not necessarily, the step for eliminating electrostatic charges is carried out after the piercing step. One interest is to be able to ionize the air contained inside the wells.

Advantageously, the step for filling the wells is carried out with at least one pipette, and during said filling step, said pipette extends coaxially to one of the wells.

One interest is to prevent the end of the pipette from coming into contact with droplets of reagent that can be located on the inner wall of the well, and therefore to avoid any contamination of the pipette.

According to the invention, a complementary manner of avoiding the contamination of the pipette is to place the lower end of the pipette slightly below the cap during the filling step. Preferably, the lower end of the pipette is placed several millimeters under the cap.

Preferably, during the filling step, an air gap is created between the poured liquid and another liquid previously present in the wells. In other words, an air gap is created between the reagent contained in each of the wells and the poured doses.

Lastly and advantageously, the method according to the invention also includes a step of verifying the positioning of the liquid poured at the end of the filling step. One primarily verifies the proper production of the air gaps.

BRIEF DESCRIPTION OF THE DRAWINGS

The invention will be better understood and its advantages will better appear upon reading the following detailed description, of an embodiment illustrated as a non-limiting example. The description refers to the drawings, in which.

DETAILED DESCRIPTION

Figure 1:
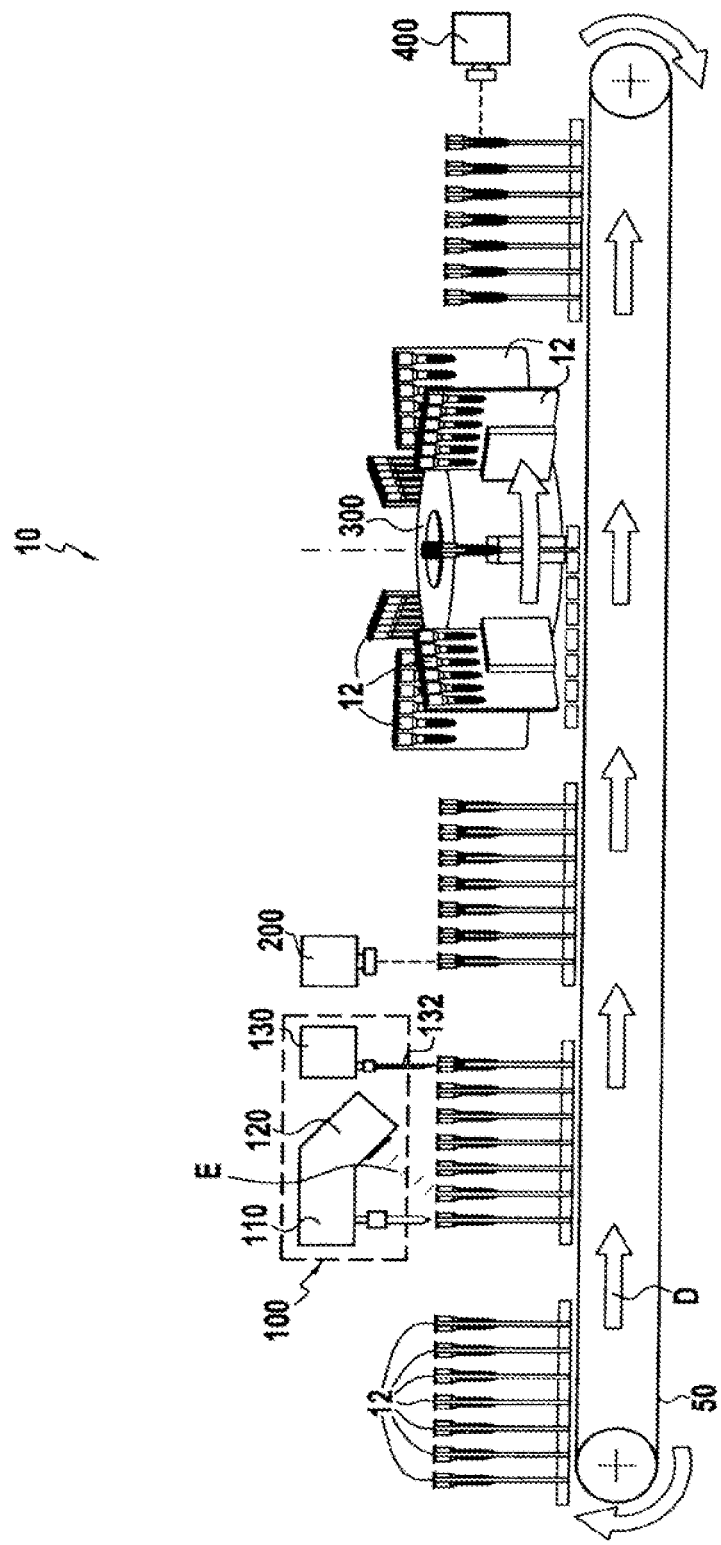
FIG. 1 diagrammatically illustrates a medical analysis machine according to the invention, which includes a filling device according to the invention.

FIG. 1 shows a very diagrammatic and non-limiting illustration of a medical analysis machine 10 according to the invention.

Figure 2:
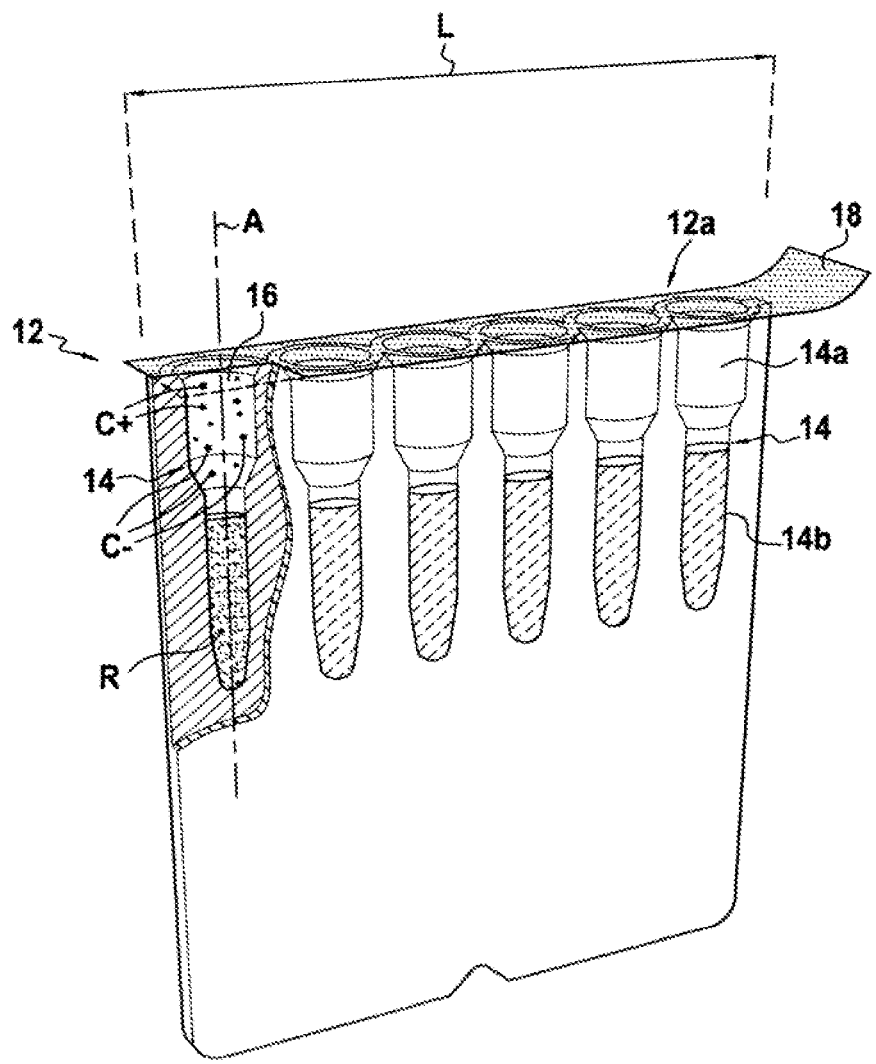
FIG. 2 is a frontal view of a receptacle intended to be used with the machine of FIG. 1.

This machine 10 uses consumable receptacles, in this case gel cards 12 provided with wells 14, also well known. FIG. 2 shows that each of the gel cards 12 of this example includes six wells 14 emerging in an upper wall 12a of the gel card. These wells 14 therefore have openings 16 formed in the upper wall 12a of the gel card, these openings 16 initially being sealed by a cap 18 that extends in a longitudinal direction L of the gel card 12. In that example, the cap 18 consists of a thin strip sealed to the upper wall of the gel card 12.

As understood using FIG. 2, each well 14 of the gel card 12 contains, in a known manner, a reagent R, said reagent being able to be different from one well to the next.

More specifically, each well 14 is formed by a substantially cylindrical upper cavity 14a connected to a lower cavity 14b that is also substantially cylindrical via a tapered intermediate cavity. The upper cavity 14a has a diameter substantially larger than that of the lower cavity 14b, and the upper 14a and lower 14b cavities are coaxial with a shared axis A. As shown in FIG. 2, the reagent is contained in the lower cavity 14b, the reagent level being situated slightly below the upper end of the lower cavity 14b, while the upper cavity 14a, initially empty, emerges in the upper wall 12a of the gel card 12.

It happens that the gel cards 12, made from plastic, have a propensity to bear electrostatic charges C+, C−; it is thought that they are generated during impacts that the gel cards 12 may undergo during handling thereof.

Referring again to FIG. 1, one sees that the machine includes a conveyor 50 that makes it possible to move the gel cards 12 of the machine 10 in an intake direction D. Of course, any other type of conveyor can be used without going beyond the scope of the present invention.

Considered in the intake direction D, the machine 10 successively includes a filling device 100 according to the invention, an audit station 200 to verify the position of the liquid poured into the wells by the filling device, a compressor impeller 300, then means 400 for analyzing the chemical reactions likely to occur in the wells of the gel card.

The gel cards 12 are first conveyed toward the filling device 100, the latter being intended to fill the wells of the gel cards 12 with a liquid in a predetermined quantity.

To that end, the filling device 100 according to the invention first includes a piercing member 110 to perforate the caps 18 of the gel cards.

According to one essential aspect of the invention, the filling device 100 also includes means 120 for eliminating the electrostatic charges that may be borne by the gel cards. And of course, the filling device also includes filling means 130 to fill the wells of the gel cards after perforation of the cap and elimination of the electrostatic charges. It is specified that, according to the preferred embodiment of the invention, the filling means 140 are automatic. However, and without going beyond the scope of the present invention, they may also be made up of a manual pipette handled by an operator.

The piercing member 110 and the means 120 for eliminating the electrostatic charges will first be described in more detail using FIGS. 3 and 4.

The piercing member 110 includes a piercing rake 112 that is provided with six tips 114, these tips being intended to penetrate the wells of the gel card while passing through the cap 18 so as to create a series of holes 17 in the cap. The gel cards 12 also including six wells 14, it is understood that the rake 112 makes it possible to produce six holes 17 at once in the cap of each of the gel cards 12.

Figure 3:
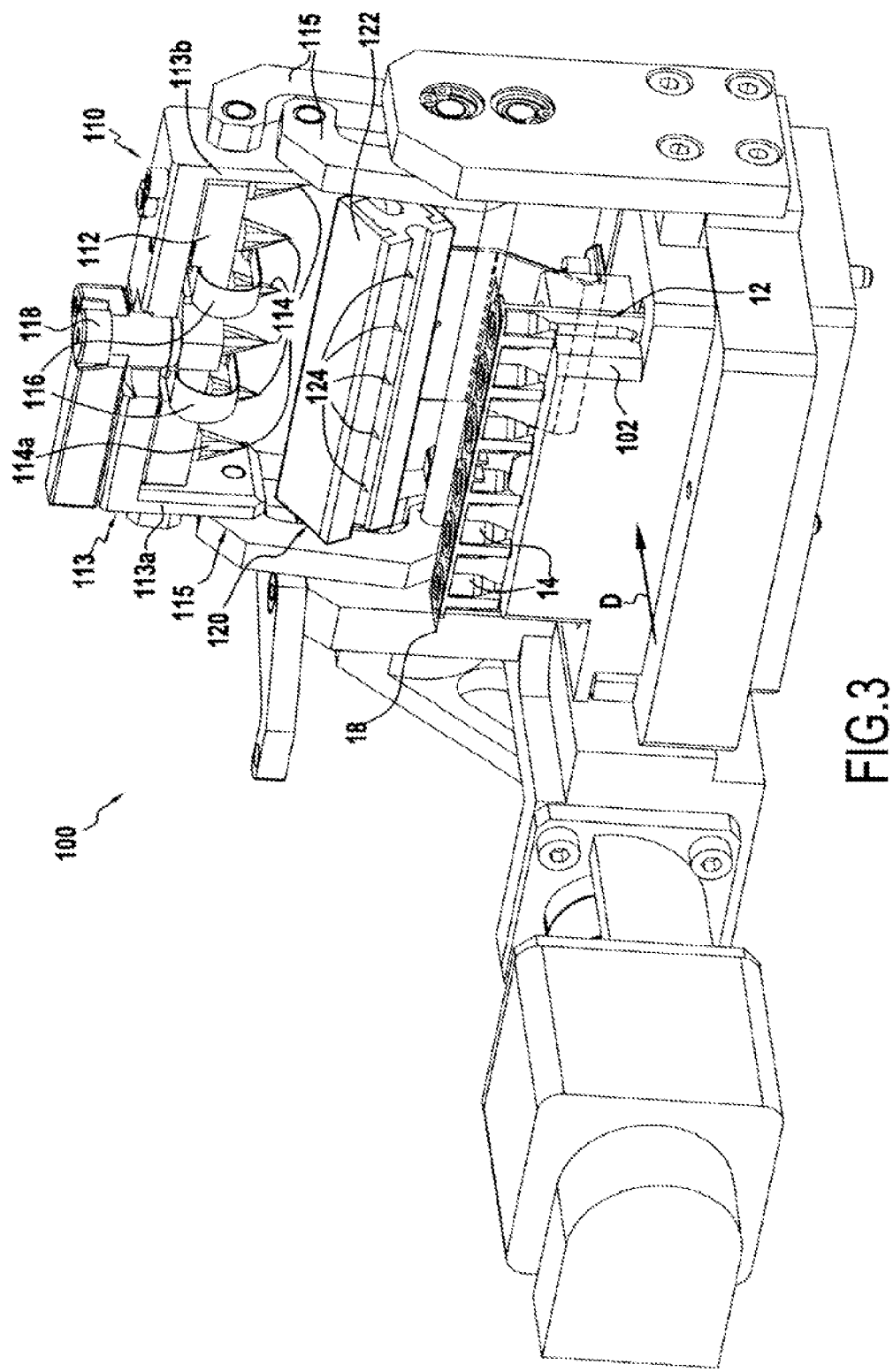
FIG. 3 is a perspective view of one preferred embodiment of the filling device according to the invention.

As seen in FIG. 3, this rake 112 extends transversely relative to the intake direction D.

What is more, the tips 114 of the rake 112 preferably have flats 114a in order to favor the piercing of the cap 18.

Furthermore, a pair of spring blades 116 extending between the tips 114 is provided to facilitate the disengagement of the piercing rake 112 after perforating the cap 18.

Lastly, it is specified that the rake 112 is locked to a rake holder 113 by a locking member 118 making it possible to disassemble the rake 112. Furthermore, this rake holder 112 includes two mobile arms 113a, 113b between which the rake 112 extends, these arms being connected to pivoting connecting rods 115 that make it possible to bring the rake 112, following a circular translational movement, from an idle position (shown in FIG. 3) toward a working position in which the tips 114 perforate the cap 18 of the gel card.

According to one advantageous aspect of the invention, the means 120 for eliminating the electrostatic charges comprise an ionizer 122 here made up by an ionization ramp that is powered by traditional power means not shown here.

This ionization ramp 122 is immobile relative to the machine and extends transversely relative to the intake direction D between the arms cavities 113a and 113b of the rake holder 113. As seen in FIG. 3, the ionization ramp 122 is situated below the tips 114 of the rake 112 when the latter is in its idle position. Said ramp 122 is also arranged so that the tips 114 of the rake 112 do not touch the rake during movement of the rake 112 toward its working position.

Furthermore, FIG. 3 shows that the ionization ramp 122 includes several electrodes 124, in this case five, protruding from the bottom of a longitudinal groove 126.

Figure 4:
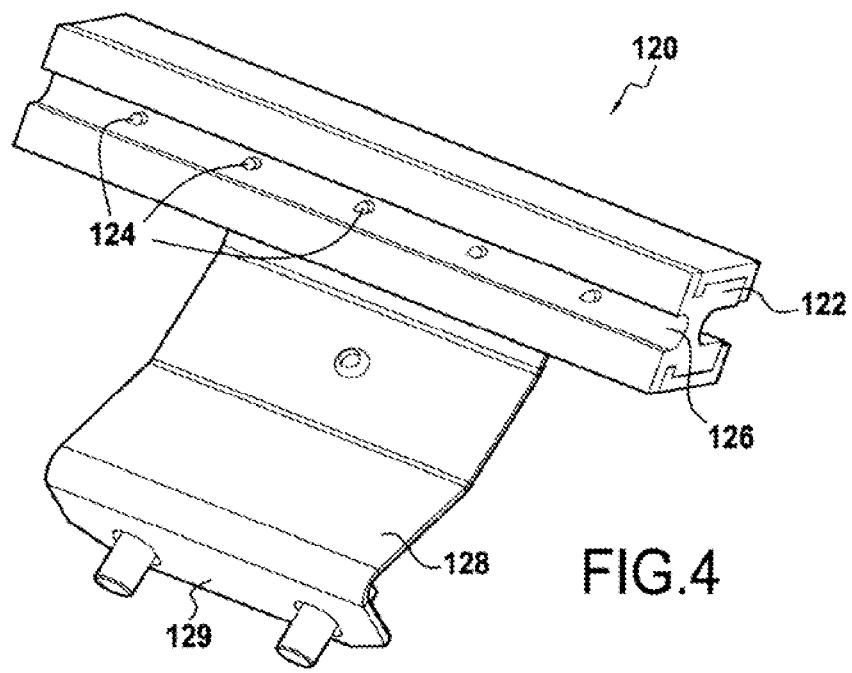
FIG. 4 is a detailed view of the ionization ramp of the filling device of FIG. 3.

In reference now to FIG. 4, one can see that the ionization ramp 122 is mounted on a holder 128 having a fastening foot 129. The ramp is tilted by about 60° relative to the vertical so that the electrodes 124 of the ramp target a zone in which the gel card is located during the piercing operation of the cap 18. Preferably, the distance between the ionization ramp and the openings 16 of the wells 14 is between 15 and 30 mm. In this particular case, the electrodes 124 of the ionization ramp 122 serve to generate an electrical field E, of the corona type, around wells 14 of the gel card 12. To that end, one can for example choose a power supply of the auto-transformer type delivering a sinusoidal wave, with a frequency of 50 Hz, with a potential difference of 4 KV and fan-out of 2.5 mA on each electrode.

We will now explain the filling method used by the filling device 100 according to the invention.

As shown in FIG. 3, the gel cards 12 are successively brought near the piercing member 110, in a housing 102 extending transversely relative to the intake direction D, so that, during the piercing operation, the gel card 12 is maintained in a vertical plane transverse to the intake direction D.

When the piercing member 110 is actuated, the rake 112 tilts in its working position following the circular translational movement described above, so that the tips 114 of the rake 112 perforate the cap 18. Then, the rake 112 is brought back into its idle position as shown in FIG. 3. At the end of the piercing step, the cap 18 is pierced with six holes 20 at the wells 14.

After this piercing step, the ionization ramp is activated so as to generate an electrical field with a corona effect around the wells 14. As explained above, this corona effect electrical field generates ionized air that results in eliminating the electrostatic charges C+, C− that may be borne by the wells of the gel cards 12. Preferably, the ionization duration of the wells 14 is between 1 and 1.5 second.

After the ionization step, the gel card 12 is brought toward the filling means 170. The latter include at least one pipette 132 visible in FIG. 5. As shown in that figure, the pipette 132 is successively inserted into each of the upper cavities 14a of the wells 14 through the holes 20 formed in the cap 18 following the piercing operation. During the insertion of the pipette into one of the wells 14 through the hole 20, the lower end 132a of the pipette is brought to several millimeters below the cap, while the pipette is arranged coaxially relative to said well.

Figure 5:
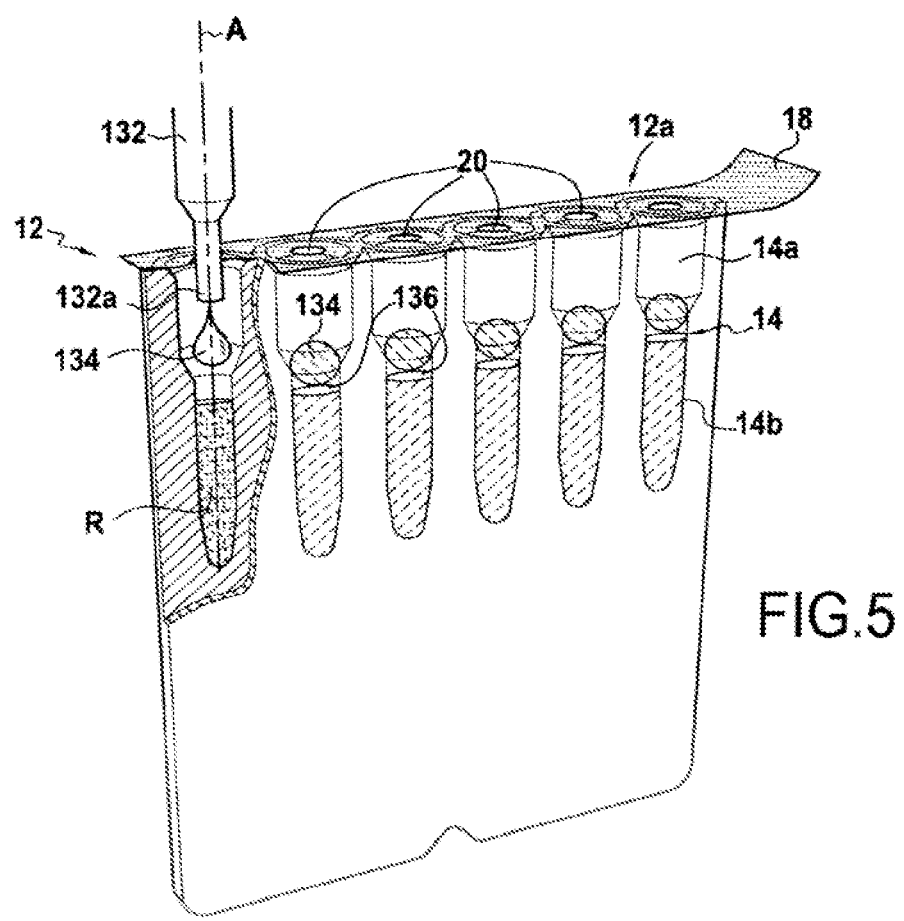
FIG. 5 shows the formation of an air gap between the reagent contained in a well of the receptacle of FIG. 2 and a dose of liquid dispensed by a pipette of the machine of FIG. 1.

Then, the pipette 132 pours a dose 134 of liquid, that is to say about 10 μm, into the upper cavity 14a, as shown in FIG. 5 for the wells situated close to the left edge of the gel card 12.

Very preferably, an air gap 136 is created between the dose 134 and the reagent contained in the lower cavity 14b of the wells 14. This air gap is situated essentially below the tapered intermediate cavity.

At the end of the filling step, the gel card 12 is brought into the checking station 200 in order to verify the presence of air gaps 136.

After this, the gel card 12 is incubated, then centrifuged owing to the compressor impeller 300.

The result of the chemical reactions taking place in the wells 14 is then analyzed using means 400 for analyzing chemical reactions. Such means, otherwise known, generally include a reader making it possible to visualize the result of the reaction(s) in the wells 14 of the gel card 12.

The invention claimed is:

1. A method of filling a receptacle provided with at least one well initially containing one or more reagents and being sealed by a cap, said method comprising:
   a step of piercing the cap of the receptacle;
   a step of eliminating electrostatic charges borne by the at least one well after the piercing of the cap; and
   a filling step during which a liquid dose is poured into the at least one well of the receptacle after elimination of the electrostatic charges, wherein an air gap is formed between the one or more reagents and the liquid dose.

2. The filling method according to claim 1, wherein the step for eliminating the electrostatic charges consists of ionizing the at least one well of the receptacle by generating an electrical field producing a corona effect.

3. The filling method according to claim 1, wherein the filling step is carried out by means of a filling system, the filling system comprising at least one pipette, and wherein the filling step is carried out with the at least one pipette, and, during said filling step, each of said at least one pipette extends from the filling system to a respective one of the at least one well, coaxially to the respective well.

4. The filling method according to claim 3, wherein the filling system comprises at least one pipette having a lower end, and, during said filling step, the lower end is placed below the cap.

5. The filling method according to claim 1, further comprising a step of verifying the positioning of the liquid dose poured into the at least one well during the filling step.

6. The filling method according to claim 1, further comprising a step of transporting the receptacle toward the piercing member prior to the piercing step, wherein the transporting of the receptacle step defines an intake direction.

7. The filling method according to claim 6, wherein the step of eliminating electrostatic charges is performed by ionizing the receptacle with an ionization ramp that extends transversely relative to the intake direction.

8. The filling method according to claim 7, wherein the ionization ramp includes a plurality of electrodes that are configured to ionize the at least one well of the receptacle during the piercing of the cap of the receptacle.

9. The filling method according to claim 1, wherein the receptacle is a card, which includes a plurality of wells sealed by the cap, each of the wells containing at least one of the one or more reagents.

\* \* \* \* \*